United States Patent [19]

Timmons et al.

[11] 4,022,211
[45] May 10, 1977

[54] WETNESS INDICATOR FOR ABSORBENT PADS

[75] Inventors: Terry K. Timmons; Dan D. Endres, both of Appleton, Wis.

[73] Assignee: Kimberly-Clark Corporation, Neenah, Wis.

[22] Filed: Oct. 8, 1975

[21] Appl. No.: 620,659

Related U.S. Application Data

[63] Continuation of Ser. No. 497,475, Aug. 14, 1974, abandoned.

[52] U.S. Cl. .......................... 128/287; 116/114 R
[51] Int. Cl.² .................................. A61F 13/16
[58] Field of Search .......... 128/284, 287, 288, 286, 128/290 R, 296; 116/114 AM, 114 R, 114 AJ

[56] References Cited

UNITED STATES PATENTS

| | | | |
|---|---|---|---|
| 2,249,867 | 7/1941 | Snelling | 116/114 AM X |
| 3,675,654 | 7/1972 | Baker et al. | 128/287 |
| 3,702,610 | 11/1972 | Sheppard et al. | 128/284 |
| 3,759,261 | 9/1973 | Wang | 128/287 |
| 3,844,718 | 10/1974 | Cohen | 116/114 AM X |
| 3,952,746 | 4/1976 | Summers | 128/287 |

Primary Examiner—Clifford D. Crowder
Attorney, Agent, or Firm—Daniel J. Hanlon, Jr.; William D. Herrick; Raymond J. Miller

[57] ABSTRACT

A wetness indicator for an absorbent pad assembly in which the pads have light-transmitting backing sheets. The indicator comprises a water-dispersible or water-soluble coloring agent affixed to a carrier means adjacent the absorbent pad and of sufficient intensity to be readily visible through the backing sheet when the pad is dry but which after being wetted by aqueous body fluids becomes substantially invisible. The coloring agent may be used by itself or with a suitable binder. It may also be used alone or in combination with a permanent color pattern or design which latter remains visible after wetting.

19 Claims, 6 Drawing Figures

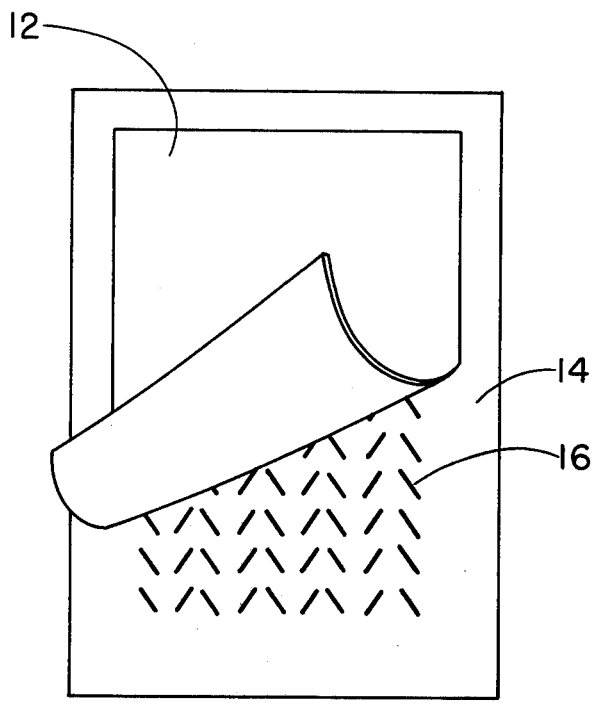
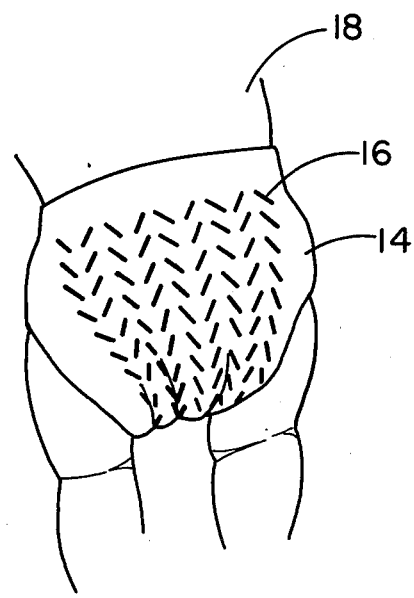
FIG. 1
FIG. 2
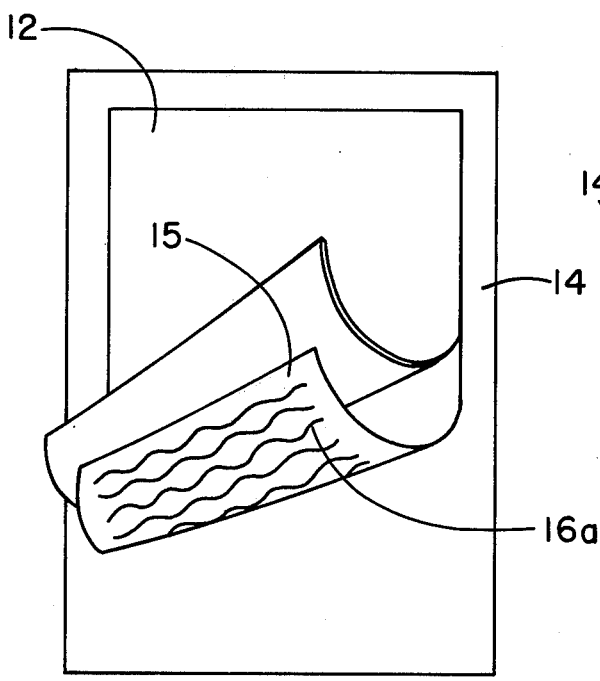
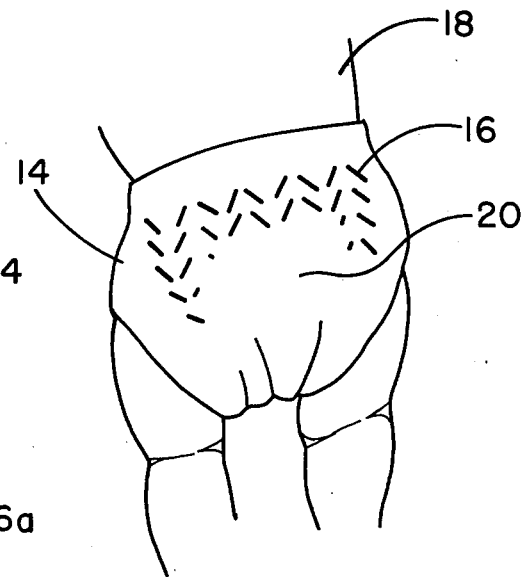
FIG. 4
FIG. 3

4,022,211

WETNESS INDICATOR FOR ABSORBENT PADS

This is a continuation, of application Ser. No. 497,475 filed Aug. 14, 1974. now abandoned.

BACKGROUND OF THE INVENTION

This invention relates to indicator means for an absorbent pad assembly, and particularly disposable diapers, which visually signals the user when the pad is wetted by aqueous fluids to assist the user in determining whether or not a fresh pad is needed.

In the prior art a number of such indicators are disclosed for that purpose. However all of these rely on systems wherein the indicator is initially not visible or is temporarily masked. These prior art indicators become visible only after the pad is wetted.

For example, Baker et al U.S. Pat. No. 3,675,654 of July 11, 1972 utilizes an indicator agent which is disposed between a translucent backing sheet and an absorbent pad and comprises either a small amount of finely divided water-soluble dye having a high dye strength of such a dye admixed with a finely divided diluent masking agent such as talcum powder. The indicating agent is applied in dry form and adheres to the pad surface facing the backing sheet where it is substantially invisible through the backing sheet. When the pad and the agent becomes wet from an aqueous body fluid the dye becomes visible through the backing sheet.

Wang U.S. Pat. No. 3,759,261 of Sept. 18, 1973 utilizes an internal layer carrying a printed pattern which is covered by another layer of sufficient density to conceal the printed pattern when the diaper is dry but which when wetted permits the printed pattern to become readily visible.

While each of these perform the desired function of indicating diaper wetness, it was found that some mothers were not in favor of using a system because is also signalled to everyone else that their child was wet and needed changing. A more discreet, less conspicuous means for indicating wetness appeared desirable.

The present invention utilizes such an approach. It provides a wetness indicator while the diaper is dry shows a decorative color or printed pattern through the backing sheet. When a diaper is wetted this color or pattern quickly fades and then substantially disappears from view.

The principle employed in the invention is similar to one found in Sheppard et al U.S. Pat. No. 3,702,610 of Nov. 14, 1972 which teaches the use of a colored water-dispersible adhesive binder for non-woven wrappers which when dropped in the excess water of a toilet is gradually dissolved and dispersed by the water whereby the color migrates away from the bonded areas into adjacent unbonded areas to indicate that the bonded areas are dissolved and that the wrapper is ready for flushing. However, the Sheppard et al indicator system is used for an entirely different function and purpose than that which will be defined herein.

SUMMARY OF THE INVENTION

In the present invention, an absorbent assembly comprising an absorbent pad and a fluid-impervious light-transmitting backing sheet in association therewith has disposed between the pad and backing sheet a wetness indicator in the form of a coloring agent of sufficient color-intensity to be visible through the backing sheet when the pad is dry. The wetness indicator is a water-dispersible coloring agent temporarily affixed to a carrier means disposed at the interface of the pad and backing sheet. A preferred coloring agent is a water-soluble non-toxic dye in a water-dispersible binder.

The carrier means is preferably the backing sheet and a solid or intermittent pattern of the coloring agent is affixed to that side of the backing sheet which faces the pad. A separate absorbent fiber sheet may also be used as the carrier means. When the pad is wetted by body fluids, the coloring agent is dispersed or dissolved, and transported by the fluid from the carrier means into the pad so that it is no longer visible through the backing sheet. The degree and area of color disappearance indicates the degree and area of wetness in the pad. An additional embodiment is the use of a permanent color or pattern in areas adjacent the disappearing color or pattern, the permanent color being unaffected by wetting. This latter modification serves to make the color change less obtrusive or discernible to other persons while still signalling the user that a change is desirable.

The invention is primarily adaptable to disposable diapers but may be used in other absorbent assemblies where wetness indicators are appropriate such as burn dressings, medical bandages, incontinent pads, sanitary napkins and the like.

The above features and advantages of the invention as well as others will become apparent from the following detailed description and accompanying drawings.

BRIEF DESCRIPTION OF THE DRAWINGS

In the drawings:

FIG. 1 is a plan view of an absorbent assembly utilizing the invention in a simplified diaper structure in which the absorbent pad portion is partly turned back.

FIG. 2 is a partial rear view of the diaper structure of FIG. 1 in place on the torso of a child and showing the appearance of the diaper in dry condition.

FIG. 3 is a view similar to FIG. 2 in which the diaper has been wetted.

FIG. 4 is a plan view similar to FIG. 1 but showing another form of the invention.

DESCRIPTION OF THE PREFERRED EMBODIMENTS

Figure 5:
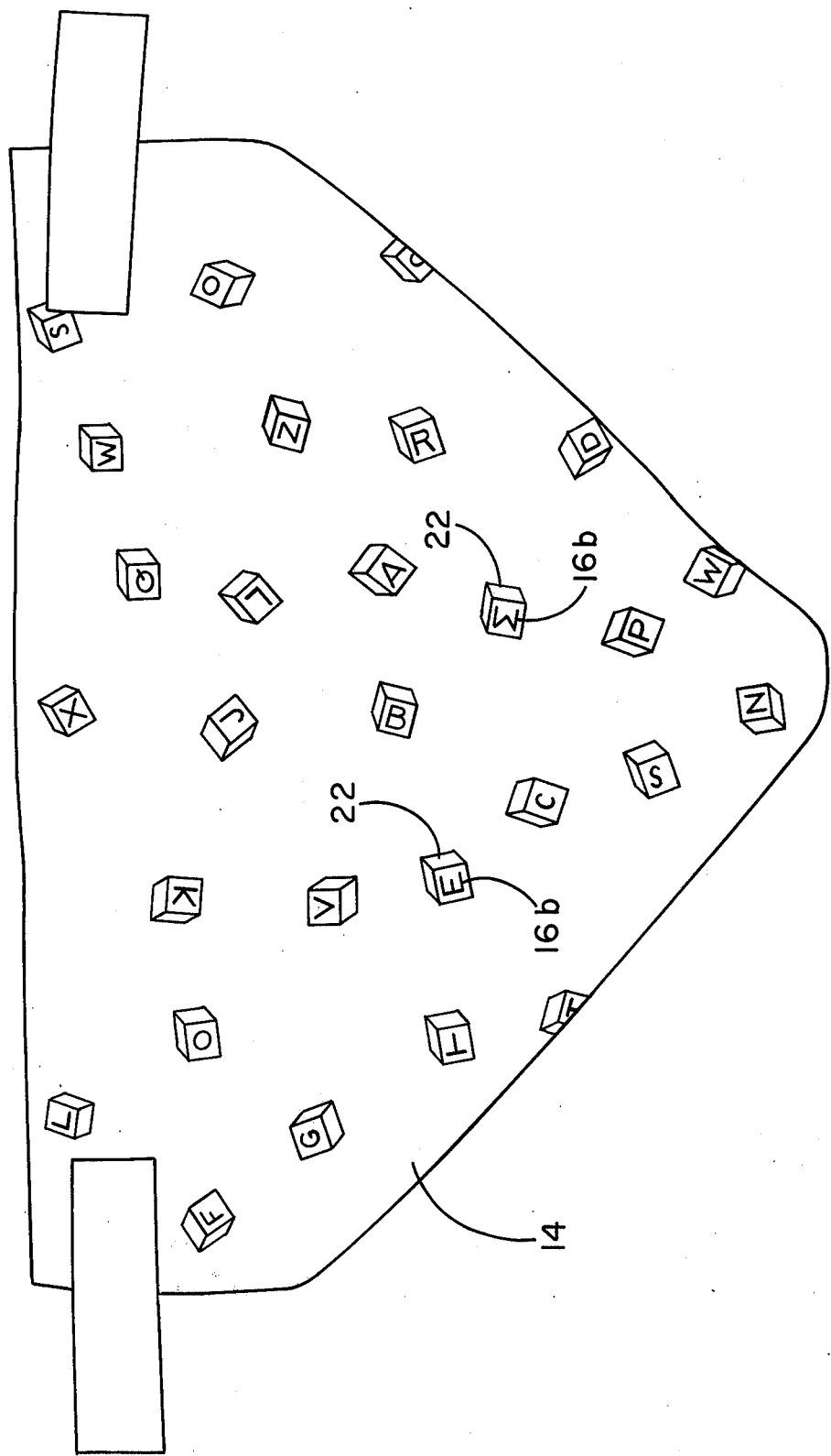
FIG. 5 illustrates the use of a decorative pattern on a prefolded triangular diaper in another embodiment of the invention.

Referring to FIG. 1 of the drawings, there is illustrated a simplified version of a disposable diaper showing a preferred embodiment of the invention. As shown therein, the diaper comprises an absorbent pad 12 which consists of suitable absorbent materials such as wood pulp fibers, multiple plies of cellulose wadding, absorbent cotton, rayon fibers and the like. This pad is disposed on a water-impervious light transmitting backing sheet 14 which preferably is of translucent or transparent plastic film such as polyethylene. The pad is usually covered by a moisture-pervious cover sheet such as a non-woven fiber web of carded rayon fibers or the like. However, the use of a cover sheet is not essential to the invention. In the FIG. 1 embodiment, that side of backing sheet 14 which faces absorbent pad 12 has affixed thereto a pattern of a water-soluble coloring agent 16, in this instance shown as a discontinuous herringbone pattern. The interior face of the backing sheet thus serves as the carrier means for the coloring agent 16. A preferred form of this coloring agent is a water-soluble dye in a water-soluble polyvinyl alcohol binder.

In FIG. 2, the diaper of FIG. 1 is shown in position on the partially-illustrated torso of a child 18. As indicated in FIG. 2 the pattern of coloring agent 16 is clearly visible through backing sheet 14 and will remain in this condition as long as the absorbent pad is dry. When the pad becomes wetted with urine, that portion of the patterned coloring agent 16 which is in contact with the wetted area is dissolved by the urine and had disappeared from view as shown at area 20 in FIG. 3 where the pattern is no longer visible. The pattern has disappeared only in that area where the pad is wetted.

FIG. 4 illustrates another embodiment of the invention in which a separate carrier means for coloring agent is employed. In this embodiment, in addition to the absorbent pad 12 and light transmitting back sheet 14 of FIG. 1, a thin absorbent sheet 15 is disposed between pad 12 and back sheet 14. That side of absorbent sheet 15 which faces back sheet 14 is imprinted with a water-soluble coloring agent 16a in a wavy line pattern. This coloring agent is of sufficient intensity in its dry condition to clearly show through back sheet 14 as in FIG. 2. When this coloring agent is wetted, it also disappears only in the wetted area as illustrated in FIG. 4. When a supplementary absorbent sheet 15 such as a cellulose tissue, a non-woven web, a thin foam sheet, or the like is employed, the coloring agent 16a may be affixed thereon by applying the agent in the form of an aqueous solution which is subsequently dried, or in the form of an aqueous dispersion in association with a water-soluble binder. When a cellulose base sheet is used as the carrier means, the coloring agent or dye employed should be one which preferably is not specific to cellulose in order that the agent will migrate easily with the body fluid when wetted. Many acid dyes are suitable for the latter purpose while some basic and direct dyes are not.

Figure 6:
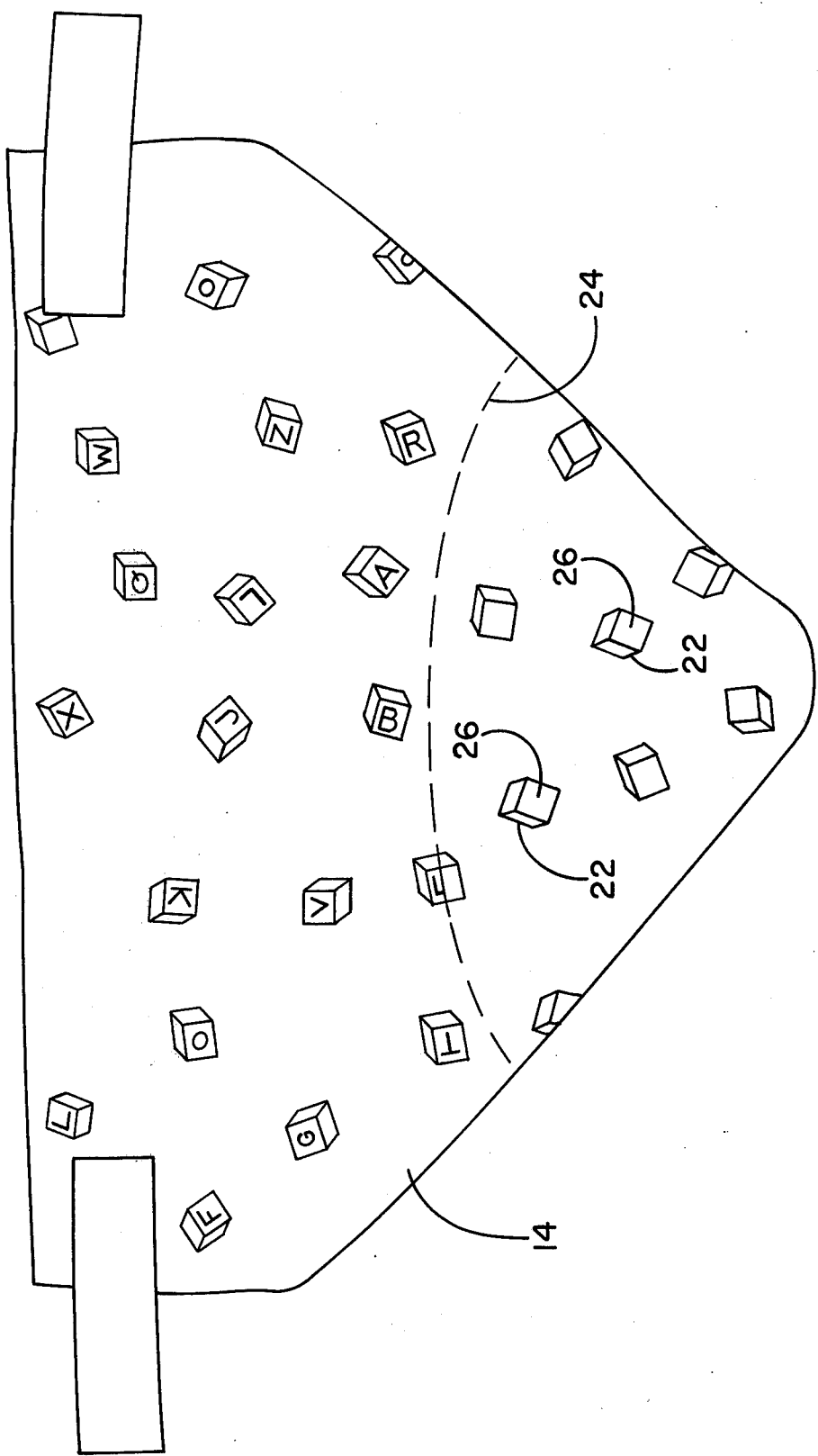
FIG. 6 illustrates what happens to a pattern similar to that in FIG. 5 after it has become wetted in a particular area.

In FIGS. 5 and 6 there is shown an additional embodiment of the invention in which a more decorative pattern is used and in which only a part of the original pattern disappears when wetted. In that embodiment a set of alphabet blocks is depicted as being printed on the inside of backing sheet 14 in scattered array. The outline 22 of each of the blocks is printed in a permanent ink or dye which will not dissolve when wetted by body fluids. The alphabet letters on the blocks are printed with the water-dispersible or water-soluble coloring agent 16b. The design is illustrated as it would appear on a prefolded triangular diaper. When the diaper pad is interiorly wetted in the area enclosed below dotted line 24, as shown in FIG. 6, the water-soluble letters will disappear as at 26 while the outline of the blocks 22 will remain visible.

It will readily be seen that the coloring agent may be applied in an unlimited variety of decorative patterns in this embodiment, with a portion of the pattern consisting of a permanent coloring agent while the other portion comprises the water-dispersible coloring agent. Contrasting colors are preferred, but monochrome may also be used.

The following specific examples of the invention which were tested in both actual use tests and bench tests will more clearly illustrate its utility.

In one example, large daytime size commercial diapers having a translucent backing sheet of 1 mil thick, white-pigmented taffeta-embossed polyethylene were used for the tests. The diapers were prepared by pre-printing the interior side of the polyethylene back sheet with a water-soluble ink in the discontinuous diamond pattern somewhat like the herringbone pattern shown in FIG. 1 of the drawings. The ink was formulated from a 50% solution of Cascorex EA 9065, a polyvinyl alcohol from Borden Adhesives diluted with distilled water. To this was added 0.1% by weight of GAF Neptune Blue BRA dye. The solution was applied to the interior face of the polyethylene by flexographic printing in the selected pattern. The test diapers were otherwise not modified in any other way from their usual commerical form. A number of these test diapers were applied to a group of children of varying age and size. The diapers were checked periodically to determine if they were wet or dry. When there was no visible change in the pattern the diapers were always found to be dry. It was also found flexing of the backing sheet in normal use did not disrupt the pattern and body perspiration had no effect on it. When visual observation of the test subjects showed that a portion of the pattern disappeared, a check of the diaper indicated that the wetted out area substantially coincided with the area in which the pattern had disappeared. Similarly, the area where the pattern did disappear always coincided with the wetted area. Thus wetness indicator as described herein not only signalled wetness but also indicated to some extent the degree and the area of wetting.

In another example, a set of diapers were prepared with a two coloring pattern similar to the style shown in FIGS. 5 and 6 printed on the interior face of the polyethylene backing sheet. The outlines of the alphabet blocks shown therein were printed on the polyethylene film with a flexographic press using a standard permanent polyethylene ink in a pink color (PMS 150 from Inmont Corporation). The film had previously been given a corona discharge treatment leaving a surface energy of about 35 dynes. The letters on the blocks were printed with a solution comprised of 50% water, 50% of water-soluble polyvinyl alcohol (Cascorex EA 9065, about 8% solids from Borden Chemical Company) colored with a tissue dye (Sky Blue 6BX a direct dye from E. I. DuPont Company) in the amount of 0.5% by weight. Each color covered about 3% of the total sheet area.

Diapers constructed with this printed polyethylene employed as the backing sheet were tested in a fashion similar to that described in the previous example. In each instance when a diaper was wetted, the letters printed on the blocks in the form of the water-dispersible Sky Blue 6BX dye disappeared in the wet-out areas while the outline of the alphabet blocks printed in the form of the permanent PMS 150 pink were unaffected and remainded clearly visible. The wetness indicator was effective for a wide range of fluid additions, and in the tests signalled wettings of less than 15 grams of urine to as much as 150 grams or more. This variation of the invention was found to be a more subtle and less conspicuous wetness indicator means than the single pattern earlier described in which only a water-soluble color was used and where the complete pattern disappeared in the wetted area. It is noted that in this embodiment the permanent color pattern may be applied to either side of the backing sheet while the transient color pattern is applied to a carrier means on the interior of the diaper.

Both styles of wetness indicators were reported by the users as being much more desirable in their estimation than the prior art forms in which a color is made to appear rather than disappear to signal wetness.

In still another example, a tissue sheet of wet strength creped cellulose wadding was printed with a plain aqueous solution of an acid dye Dupont Orange 2 and inserted between the absorbent pad and back sheet as shown in FIG. 4. The color was applied in sufficient intensity to show through the light-transmitting backing when dry. When this diaper was tested by wetting areas of the pad, it was found that the color which originally showed through the backing sheet 14 when dry also disappeared when wetted as in the other examples. In this embodiment, the contrast between wet and dry areas, while readily discernible through the backing sheet and serving satisfactorily as a wetness indicator, was not as sharp as when the coloring agent was applied directly to the film backing. Accordingly, the latter embodiment is preferred.

It should also be noted that a permanent color pattern may also be applied to the supplementary absorbent sheet if desired to provide a more decorative effect. The permanent color pattern may also be applied to the backing sheet while the transient coloring agent is applied to the supplemental absorbent sheet.

In addition to the dyes named as coloring agents in the specific examples, a large variety of other water-dispersible or water-soluble coloring agents may be used. The criteria are that these coloring agents are capable or ready dissolution or dispersion in aqueous fluids; that the agents have enough color intensity to be readily visible through a light-transmitting transparent or translucent backing; and, of course, that the agent be nontoxic and non-irritating should it inadvertently contact the skin. Various coloring agents which meet these criteria include acid, basic, and direct dyes; soluble inorganic pigments; food and vegetable colors; and the like.

Some specific coloring agents in addition to those named in the specific examples include Pontamine Turquoise 8 GLP a direct blue dye, Bond yellow CS a direct yellow dye, Dupont Red 8 BLX a direct red dye, Rhodamine B Extra a basic red dye, and Paper Blue R a direct dye all from E. I. DuPont Company; and EASTACRYL dark red LA by Eastman Kodak Company. Brom Thymol Blue, Brom Phenol Blue and Methyl Orange, all acid base dyes have also been successfully tried. Many other dyes and colors are available, and the selection of one with suitable dispersibility or solubility and aesthetic values is no problem.

The coloring agent may be affixed to the carrier means either from a thick aqueous solution or from an aqueous solution containing a water-dispersible binder. The use of a binder is preferred when the coloring agent is affixed to a plastic film backing sheet.

When a binder is used to apply and affix the coloring agent to the substrate, a water-soluble polyvinyl alcohol as set forth in the examples is presently preferred because of its availability, non-toxic characteristics and ease of use. However, other water-dispersible or water-soluble binders may be used including modified cellulosics such as carboxymethyl cellulose or cellulose glycolate and other forms of methyl cellulose and glycol cellulose. Gelatins, gums, starches, dextrins and various sugars are also suitable.

The invention is applicable to disposable pads in all their various forms as long as such pads have a construction which includes a light-transmitting back sheet through which the coloring agent is visible when dry. Transparent or translucent plastic film such as pigmented or non-pigmented polyethylene, polypropylene or vinyl is the preferred form of backing sheet, but water-resistant sheet materials such as non-wovens and the like treated for water-repellancy may also be used as long as they are sufficiently light transmitting to clearly show the coloring agent therethrough. While disposable diapers are the only form of pad described in the specific examples given above, other adsorbent pad uses are contemplated, such as burn dressings, incontinent pads, sanitary napkins and medical and surgical bandages. In other words the invention is applicable to all types of absorbent pads or assemblies which are used to absorb body fluids and the like and where it is desirable to change pads after they have become wetted.

The wetness indicating means may be applied as a solid color pattern, as a connected or disconnected pattern, in a multicolor or monochromatic arrangement and over the entire planar area of the pad assembly or only in selected areas. As indicated earlier, the transient coloring agent may be used alone or in combination with, and in cooperation with, a permanent color pattern.

The coloring agent may be conveniently applied to the carrier means by printing, but other application means such as spraying, dipping, extrusion, wiping or the like may be employed.

The term water-dispersible as used herein and in the claims is meant to include coloring agents and binders which when subjected to aqueous fluids become dispersed therein and transportable therein either as a true molecular solution or as a mobile suspension which can include dispersed particles of colloidal size and larger.

What is claimed is:

1. An improved wetness indicating means in combination with an absorbent assembly in which said assembly is comprised of an absorbent pad and a light-transmitting fluid-impervious backing sheet in association with said pad, said indicating means comprising a water-dispersible coloring agent temporarily affixed to one surface of a carrier means disposed in association with, but separate from, said pad at the interface of said pad and said backing sheet, said pad being free of said coloring agent and said coloring agent being of sufficient intensity to be visible through said backing sheet when said agent is in dry condition, said coloring agent being present in an amount such that when said agent is contacted with aqueous fluid in areas where said pad becomes wetted out due to absorption of said fluid in said pad areas during use, that portion of said agent which is contacted by said fluid in said wetted out pad areas disperses in said fluid and is transported by said fluid away from said carrier means into said wetted out pad areas whereby the dispersed portion of said coloring agent is no longer visible through said backing sheet, the degree and area of the visual disappearance of said agent indicating the degree and area of wetness in said pad.

2. The wetness indicating means of claim 1 wherein said coloring agent is temporarily affixed to said carrier means by a water-dispersible binder.

3. The wetness indicating means of claim 2 wherein said water-dispersible binder is polyvinyl alcohol.

4. The wetness indicating means of claim 3 wherein said carrier means also has affixed thereon a permanent color pattern.

5. The wetness indicating means of claim 2 wherein said carrier means also has affixed thereon a permanent color pattern.

6. The wetness indicating means of claim 1 wherein said carrier means is said backing sheet and said coloring agent is applied to the side of said backing sheet facing said pad.

7. The wetness indicating means of claim 6 wherein said coloring agent is temporarily affixed to said backing sheet by a water-dispersible binder.

8. The wetness indicating means of claim 7 wherein said water-dispersible binder is polyvinyl alcohol.

9. The wetness indicating means of claim 8 wherein said backing sheet also has affixed thereon a permanent color pattern.

10. The wetness indicating means of claim 7 wherein said backing sheet also has affixed thereon a permanent color pattern.

11. The wetness indicating means of claim 6 wherein the side of said backing sheet has affixed thereon a permanent color pattern.

12. The wetness indicating means of claim 1 wherein said carrier means is a thin absorbent sheet, and said coloring agent is applied to the side of said thin absorbent sheet facing said backing sheet.

13. The wetness indicating means of claim 12 wherein said coloring agent is temporarily affixed to said thin absorbent sheet by a water-dispersible binder.

14. The wetness indicating means of claim 13 wherein said water-dispersible binder is polyvinyl alcohol.

15. The wetness indicating means of claim 14 wherein said thin absorbent sheet also has a permanent color pattern affixed thereon.

16. The wetness indicating means of claim 6 wherein said thin absorbent sheet has also affixed thereon a permanent color pattern.

17. The wetness indicating means of claim 12 wherein a permanent color pattern is also applied to the side of said thin absorbent sheet facing said backing sheet.

18. The wetness indicating means of claim 1 wherein said carrier means also has affixed thereon a permanent color pattern.

19. The wetness indicating means of claim 18 wherein said permanent color pattern is of a different color than said coloring agent.

* * * * *